United States Patent [19]

Tanaka

[11] Patent Number: 4,498,472

[45] Date of Patent: Feb. 12, 1985

[54] SMOKE MASK

[76] Inventor: John S. Tanaka, 1080 Siskiyou Dr., Menlo Park, Calif. 94025

[21] Appl. No.: 461,625

[22] Filed: Jan. 27, 1983

[51] Int. Cl.$^3$ .............................................. A61M 16/00

[52] U.S. Cl. ............................... 128/205.17; 128/728; 128/914; 128/203.28

[58] Field of Search .............. 128/914, 205.17, 205.13, 128/203.28, 206.21, 728, 204.18, 205.16; 272/99

[56] References Cited

U.S. PATENT DOCUMENTS 2,007,330 7/1935 Hicks ............................. 128/203.28
4,032,991 7/1977 Vandeweghe .
4,345,605 8/1982 Geneg ............................ 128/205.17

*Primary Examiner*—Henry J. Recla
*Attorney, Agent, or Firm*—Thomas Schneck

[57] ABSTRACT

A protective breathing apparatus for traversing toxic smoke zones, having a face mask portion covering the nose and mouth of a user in a sealed relationship to the face, a pleated flexible vessel made of a gas-impermeable material and capable of containing ambient air, and a sealed air passageway between the mask and vessel. When not in use, the vessel can be tightly compressed and reduced in size for easy portability; however, for use, the vessel can be instantly expanded, drawing at least 60 cubic inches of ambient air therein.

4 Claims, 2 Drawing Figures

SMOKE MASK

DESCRIPTION

1. Technical Field

The invention relates to a protective mask for traversing toxic smoke-filled regions.

2. Background Art

Various types of gas masks are known in the prior art. Most masks rely upon filters to remove particles from air in order to yield a breathable air mixture. However, even the most efficient filters allow a percentage of particles and/or gases to pass through. Depending upon the nature and concentration of these particles and/or gases, the air yielded by the mask may be toxic to human consumption.

In recent years, there have been spectacular hotel fires where many deaths have occurred not so much from heat as from inhalation of toxic smoke from burning synthetic materials used in upholstery, wall coverings, sealants and surface coatings. Such deaths have occurred in areas remote from flames but high in concentration of toxic smoke transported through ducting, stairwells and elevator shafts. An object of the present invention is to provide a light weight, highly portable smoke mask to escape from a toxic smoke-filled structure such as a hotel, condominium, apartment or office building, in the event of a fire.

DISCLOSURE OF INVENTION

The above object has been met by providing a protective breathing device having a self-contained ambient air supply. Briefly, a gas-impermeable, form-fitting mask is designed to fit tightly over the nose and mouth of a user. In a preferred embodiment, the mask is connected by a common air passageway to a gas-impermeable, accordion-pleated flexible vessel containing ambient air in sufficient volume to sustain a user in an alert, active condition for a period of at least seven minutes when escaping from a toxic smoke-filled environment.

BEST MODE FOR CARRYING OUT THE INVENTION

Figure 1:
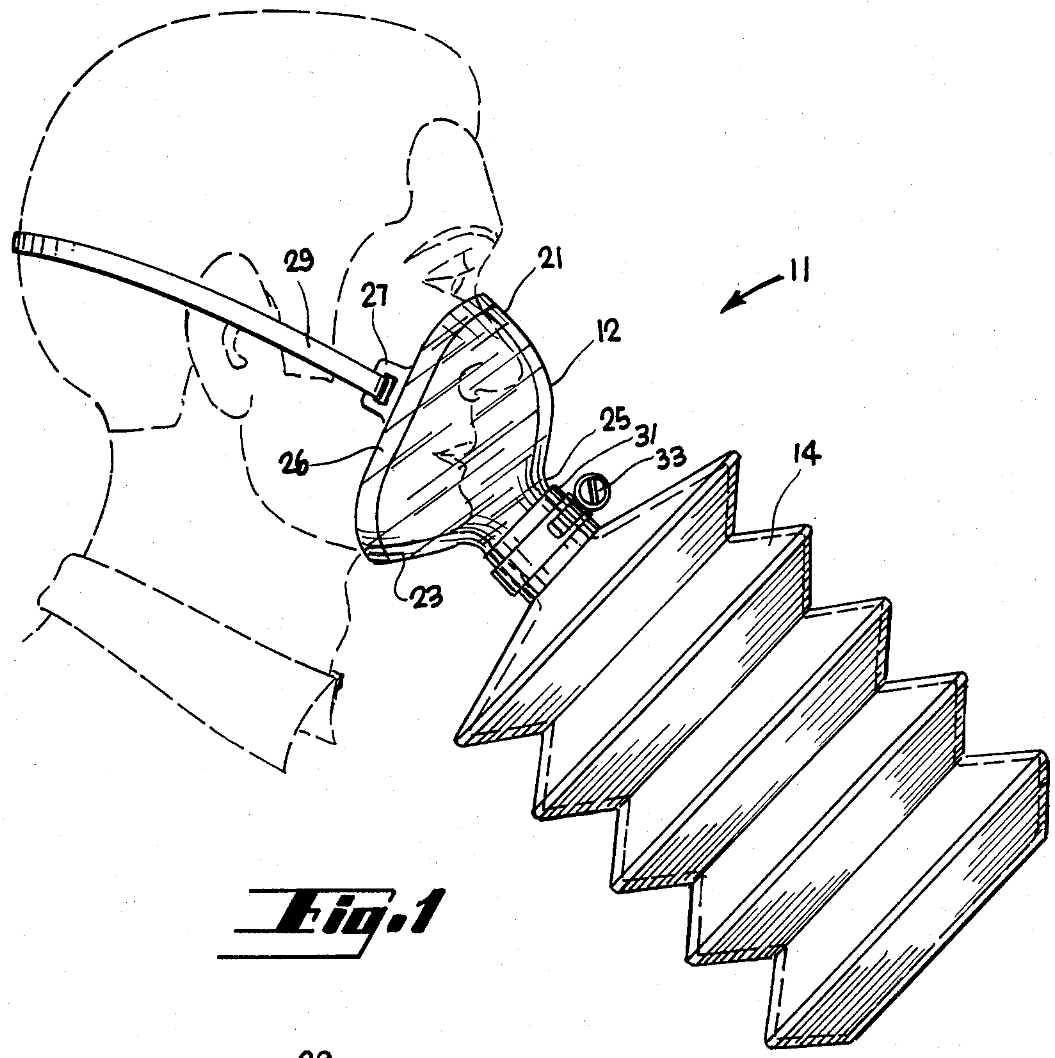
FIG. 1 is a side view of a smoke mask of the present invention when in use.

With reference to FIG. 1, the smoke mask 11 is seen to have a face mask 12 and an air supply vessel 14. Face mask 12 is form-fitting and self-supportive, and is similar in basic construction to the type used when administering oxygen resuscitation. The mask 12 includes an upper region 21 fitting over the nose and a lower region 23 fitting under the chin. A seal with the face is made by a lip 26 which is turned inwardly to contact the face, forming a seal therewith. The inwardly turned lip is approximately $\frac{5}{8}$ inches wide, more or less. The front of mask 12 has an air passage tube port 25 near the mouth region of the wearer, said port being of a tubular construction approximately 1.5 inches in diameter and of slightly longer length.

Metal or plastic clips are connected to each side of the mask 12, including a first clip 27 to which an elastic band 29 is fastened so that the mask can be easily positioned over the head of a user. A second clip on the opposite side of the mask, not visible in the figure, secures the opposite end of the band to the mask.

The mask 12 can be made of any gas-impermeable material so long as it is sufficiently pliable and deformable under pressure to adaptively fit different facial forms. The generally cylindrically shaped air supply vessel 14 is made of a thin, flexible, gas-impermeable material such as rubber, plastic or pulp-based material and has horizontal accordion pleats so that the vessel 14 can expand and contract during breathing, and fully collapse when storing. Vessel 14 has a single tubular port 31, the inner diameter of which is slightly larger than the outer diameter of tubular port 25, so that port 31 can be inserted into port 25 in a plunge fit and secured in place by adhesive or by hose clamp 33.

Figure 2:
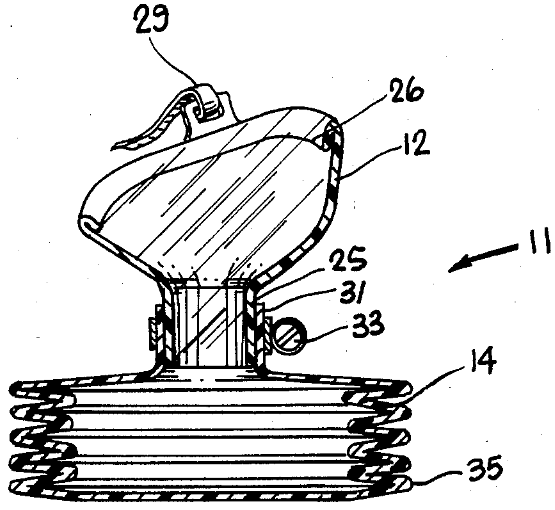
FIG. 2 is a side cutaway view of the smoke mask of FIG. 1, shown in a collapsed configuration.

With reference to FIG. 2, the mask 11 is shown with vessel 14 collapsed along its pleats and standing only a few inches tall. Face mask 12 is shown with the inwardly-turned lip 26 resting immediately above the vessel 14. It will be seen that the tubular port 25 is seated within tubular port 31, forming a substantially sealed common air passageway between mask 12 and vessel 14. The collapsed vessel 14 will take a generally cylindrical form when pulled from the vicinity of the lowermost pleat 35, simultaneously drawing ambient air therein.

The material used in the construction of mask 12 can be variable, so long as it is sufficiently flexible to adapt to different facial forms and is gas impermeable. The means of attachment to user's head is also a matter of choice since the mask of this invention can also be incorporated into a fire helmet or hood if desired and supported by such a hood.

The capacity of vessel 14, when expanded, should be at least 60 cubic inches, equivalent to about one quart. It will be readily seen that this minimum is critical. An average person, in a laboratory setup, can remain alert and active for about two minutes by recycling of the air in the person's lungs. Thereafter, the person's physical condition will deteriorate rapidly because of the progressively irrespirable quality of the air being recycled, with its rising $CO_2$ and falling $O_2$ content. Without prompt relief, the person will die of asphyxia.

The time of two minutes, fortunately, can be dramatically lengthened with the apparatus of this invention. With a reservoir of just 60 cubic inches of ambient air in vessel 14, the same person can remain alert and active for about seven minutes, said reservoir providing, of course, the $O_2$ supplement and means for diluting the $CO_2$ concentration of the air being recycled. Seven minutes is deemed minimum time to put on said apparatus and escape from the top of a tall, toxic smoke-filled structure which is on fire.

One of the advantages of mask 11 is its portability and light weight. It can be easily collapsed, stored in a case and carried, for example, in the brief case of a traveler. Another, more important advantage is its ease of correct use under substantially panic conditions. Since the user, under severe pressure, may not properly inflate vessel 14 for ambient air supply before putting on mask 11, this is done automatically. It can be seen that, with the aid of gravity, the flexible, pleated vessel 14 will hang and maintain a generally cylindrical form when the user is putting on mask 11, thereby assuring the user of having at least a minimum supply of ambient air in vessel 14 for traversing toxic smoke zones.

I claim:

1. A protective breathing apparatus comprising, a face-fitting nose and mouth face mask made of gas-impermeable material having a first air passage port, said first air passage port being the sole opening to and from said mask, a vessel having an expandible second air passage port, said second air passage port being the sole opening to and from said vessel, said vessel having a capacity, when fully expanded, of at least 60 cubic inches, said vessel made of a substantially non-porous, gas impermeable material and having a lengthwise axis with a collapsed first position and an expanded second position, said vessel having pleats compressible in the direction of said lengthwise axis and capable of retaining said vessel in said expanded position when manually extended to allow for a capacity of at least 60 cubic inches of ambient air, and a common air passageway between the face mask and vessel created by the joining of said first port and second port.

2. The apparatus of claim 1 wherein said vessel is made of a rubberized material.

3. The apparatus of claim 1 wherein the port of said mask, having a slightly smaller outer diameter than the inner diameter of the port of said vessel, is in a plunge fit relationship to each other, forming a common air passageway between said mask and vessel.

4. The apparatus of claim 1 wherein said vessel is made of a rubberized material.

* * * * *